United States Patent [19]

Swerdloff et al.

[11] Patent Number: 4,539,037
[45] Date of Patent: Sep. 3, 1985

[54] UREASE INHIBITED UREA BASED FERTILIZER COMPOSITIONS CONTAINING N-ARYL-N-ALIPHATIC PHOSPHOROTRIAMIDE COMPOUNDS

[75] Inventors: Michael D. Swerdloff, Parsippany, N.J.; Michael Van Der Puy, Cheektowaga, N.Y.; Jaroslav F. Kolc, Randolph Township, Dover County; Milorad M. Rogic, Whippany, both of N.J.; Larry L. Hendrickson, Camillus, N.Y.

[73] Assignee: Allied Corporation, Morris Township, Morris County, N.J.

[21] Appl. No.: 475,990

[22] Filed: Mar. 16, 1983

[51] Int. Cl.³ .................................................. C05C 9/00
[52] U.S. Cl. ............................................. 71/28; 71/902
[58] Field of Search ................................. 71/11, 27–30, 71/902

[56] References Cited

U.S. PATENT DOCUMENTS

| | | |
|---|---|---|
| 4,182,881 | 1/1980 | Bayless et al. .................. 546/22 |
| 4,222,948 | 9/1980 | Alaimo et al. ................. 260/397.7 R |
| 4,225,526 | 9/1980 | Alaimo et al. ................. 260/397.7 R |
| 4,242,325 | 12/1980 | Bayless et al. ..................... 424/210 |

FOREIGN PATENT DOCUMENTS 830800 3/1960 United Kingdom.
1494774 12/1977 United Kingdom.

OTHER PUBLICATIONS

1978, CA, vol. 89, Abst. #89:89455k, Matzel et al.
1979, CA, vol. 90, Abst. #90:21340j, Oertel et al.
1979, CA, vol. 91, Abst. #91:122724p, Matzel et al.
1979, CA, vol. 91, Abst. #91:139619f, Heber et al.
1981, CA, vol. 94, Abst. #94:101951g, Vlek et al.
1981, CA, vol. 94, Abst. #94:139429f, Bayless et al.

*Primary Examiner*—Ferris H. Lander
*Attorney, Agent, or Firm*—Richard C. Stewart, II

[57] ABSTRACT

The invention relates to novel urease inhibited fertilizer compositions containing urea and a urease inhibiting amount of phosphorotriamidate compounds, and methods and composition for inhibiting the activity of urease through use of such compounds.

39 Claims, 1 Drawing Figure

UREA HYDROLYZED VS TIME AT 35°C USING
10 MICROGRAMS INHIBITOR PER GRAM SOIL

O———O CONTROL
△———△ PHENYL PHOSPHORODIAMIDATE
◆—·—·—◆ N-METHYL-N-(4-NITROPHENYL) PHOSPHORIC TRIAMIDE

UREA HYDROLYZED VS TIME AT 35°C USING 10 MICROGRAMS INHIBITOR PER GRAM SOIL

○———○ CONTROL
△———△ PHENYL PHOSPHORODIAMIDATE
◆—·—◆ N-METHYL-N-(4-NITROPHENYL) PHOSPHORIC TRIAMIDE

UREASE INHIBITED UREA BASED FERTILIZER COMPOSITIONS CONTAINING N-ARYL-N-ALIPHATIC PHOSPHOROTRIAMIDE COMPOUNDS

BACKGROUND OF THE INVENTION

1. Field of the Invention

This invention relates to urease inhibited urea based fertilizer compositions. More particularly, this invention relates to urease inhibited urea based fertilizer compositions which contain certain N-alkyl-N-aryl phosphorotriamide compounds as the urease inhibitors, and to methods and compositions for inhibiting the action of soil urease through use of such compounds.

2. The Prior Art

It is well known in the art to use urea and urea compositions in fertilizers, for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonias, when urea is placed under or on the surface of moist soil which contains urease. Urease, a crystallizable enzyme occurring in numerous bacteria and fungi, as for example *Micrococcus urease*, catalyzes the conversion of urea into ammonia and carbon dioxide. The reactions are as follows:

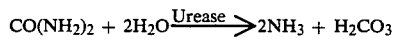

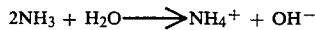

A portion of the ammonia thus formed is held by absorbing constituents of the soil and is available to plants as nutrient. However, a large amount of the ammonia may be lost to the air. A further problem resulting from the action of urease is that the accumulation of ammonium in the soil and rise in problems, including damage to germinating seedlings and young plants.

One approach to reduction of problems resulting from the activity of soil urease toward soil applied urea is to find compounds that inhibit urease activity when applied to soils in conjunction with fertilizer urea. This approach has received considerable attention, and several classes of compounds have been used as urease inhibitors.

For example, certain prior art describes various phosphoro compounds which are useful as urease inhibitors. Illustrations of such prior art are East German Pat. Nos. 142,714; 212,026; 122,177; 122,621 and 130,936, and Great Britain Pat. No. 1,494,774 describe various phosphorodiamidate compounds as urease inhibitors. Also exemplary of such prior art is U.S. Pat. No. 4,242,325 which describes a method of controlling the enzymatic decomposition of urea to ammonia and carbonic acid due to the action of urease which comprises exposing the enzyme to certain phosphorotriamide compounds. U.S. Pat. No. 4,182,881 describes the use of certain N-[diaminophosphinyl]arylcarboxyamide compounds as inhibitors of the enzyme urease in the urinary tract. U.S. Pat. No. 4,225,526 describes the use of 8-[(4-aminophenyl)sulfonyl]amino-2-napthalenyl phosphorodiamidate compounds as inhibitors of the enzyme urease, and U.S. Pat. No. 4,222,948 describes the use of [(4-aminophenyl)sulfonyl]amino]phenyl phosphorodimidates as inhibitors of the enzyme urease.

Still other prior art describes phosphorotriamidate compunds which are useful for other purposes as for example, as flame proofing agents. For example, Great Britain Pat. No. 830,800 describes certain phosphorotriamides which are useful as flame proofing agents.

SUMMARY OF THE INVENTION

In accordance with the present invention, there is provided a unique fertilizer composition comprising urea or a compound which is capable of forming urea when subjected to the use conditions of the composition and a urease inhibiting amount of one or more phosphorotriamide compounds of the formula:

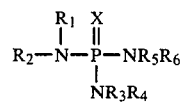

wherein:

X is oxygen or sulfur;

$R_1$ is alkyl, alkenyl, alkynyl, cycloalkyl, cycloalkenyl or aralkyl;

$R_2$ is heterocycle, aryl or substituted aryl having one or more substituents selected from the group consisting of trihalomethyl, alkyl, halo, phenoxy, isocyanato, phenyl, nitro, cyano, amino, alkylamino, dialkylamino, alkoxy, arylmercapto, mercapto, alkylcarbonyl, isocyano, alkylmercapto, arylcarbonyl, carboxy, carbonamide, alkylcarboxy, $(NH_2)_2P(O)O-$, $(NH_2)_2P(O)NH-$, and $H_2NSO_2-$; and $R_3$, $R_4$, $R_5$ and $R_6$ are individually hydrogen or alkyl having from 1 to 4 carbon atoms.

Hereinafter, the aforementioned compounds are referred to as "phosphorotriamide compounds".

Another aspect of this invention relates to a method of enhancing the yield of plants which comprises applying the composition of this invention to a plant growth medium within reach of the plant's root system, (hereinafter referred to as "root zone"). The term "plant growth medium" as herein employed refers to various natural and artificial media which support plant growth, including soil, potting mixtures of organic and inorganic matter, and artificial media such a polyurethane foams.

Yet another aspect of this invention relates to a method of inhibiting the action of urease against urea applied to a plant growth medium containing the said urease, which method comprises applying to said medium a "urease inhibiting effective amount" of one or more of the above-described N-aliphatic-N-aryl phosphorotriamide compounds. Still another aspect of this invention relates to a composition comprising a "urease inhibiting effective amount" of one or more phosphorotriamide compounds, which composition is useful for carrying out the aforementioned method. As used herein "urease inhibiting effective amount" is an amount of one or more of the said N-aryl-N-aliphatic phosphorotriamide compounds which when admixed with urea (or a compound capable of forming urea in situ under the use conditions of the compound) or applied to a plant growth medium before, after or in conjunction with application of urea or one or more urea precursor compounds to the said plant growth medium is capable of inhibiting the catalytic activity of urease that may be in the medium to any extent.

It has been discovered by distributing a urease inhibiting effective amount of one or more of the N-aryl-N-aliphatic phosphorotriamide compounds in a plant growth medium the urease catalyzed hydrolysis of urea to ammonia is suppressed thereby preventing the rapid loss of urea from the medium. Furthermore, by proper distribution of the one or more N-aryl-N-aliphatic phosphorotriamide compounds this action of inhibiting the urease catalyzed hydrolysis of urea to ammonia is effective over a prolonged period of time.

DETAILED DESCRIPTION OF THE INVENTION

Figure 1:
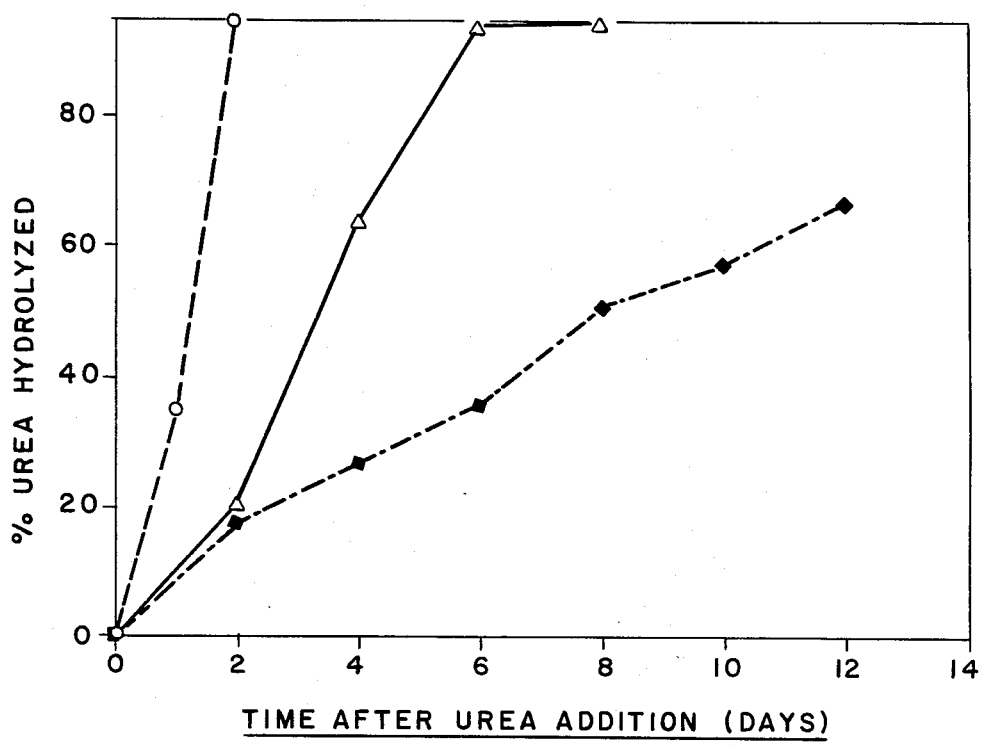
FIG. 1 is a graph of urea hydrolyzed vs. time at 35° C. using 10 micrograms of urease inhibitor per gram of soil.

The application and/or distribution of a urease inhibiting effective amount of one or more of the above-identified phosphorotriamide compounds to a plant growth medium is essential for the practice of this invention. Preferably, the amount of the phosphorotriamide compounds employed is sufficient to inhibit the urease catalyzed hydrolysis of substantially all urea present in the composition. Usually, an acceptable level of urease inhibition can be achieved if the composition contains at least about 0.01 parts by weight of said one or more phosphorotriamide compounds per one million parts by weight of soil or other plant growth medium. Hereinafter the abbreviation "p.p.m." is used to refer to parts by weight of one or more phosphorotriamide compounds per one million parts by weight of plant growth medium. In the preferred embodiments of this invention, the amount of said one or more phosphorotriamide compounds distributed in the said medium is from about 0.01 p.p.m. to about 5,000 p.p.m., and in the particularly preferred embodiments of the invention is from about 0.2 p.p.m. to about 1,000 p.p.m. Amongst these particularly preferred embodiments of the invention, most preferred are those embodiments of the invention in which the amount of said one or more phosphorotriamidate compounds distributed in said medium is from about 1 p.p.m. to about 500 p.p.m.

Within the aforementioned limitations, the preferred amounts of the one or more phosphorotriamide compounds impregnated or distributed in the plant growth medium are dependent upon the particular situation. Thus, in determining the amount to be employed, consideration is made not only of the treatment need, i.e., soil pH, temperature, soil type, etc., but also of the mode of application to soil. When the one or more phosphorotriamide compounds are to be applied in a broadcast application, the amount in p.p.m. may frequently be less than in row or band application where, for a substantial depth and width within the vicinity of application, there can be a very high concentration of the one or more such compounds. When application is made near the root zone or growing plants or when application is made immediately prior to seeding or transplanting, the amounts supplied are frequently at a lower rate than when application is made at the end of the growing season to prepare the soil for the following season. By dispersing very large dosages in growth media, a prolonged inhibition of urease activity can be obtained over a period of many months. The concentration of the one or more phosphorotriamide compounds is eventually reduced to a minimum by decomposition in the soil.

In one method for carrying out the present invention, one or more phosphorotriamide compounds are distributed throughout the plant growth media in a broadcast application such as by spraying, dusting, distributing in irrigation water and the like. In such application, the one or more phosphorotriamide compounds are supplied in amounts sufficient to permeate the growing area of soil with a urease inhibiting effectaive amount of such phosphorotriamide compounds. In field administration, the one or more phosphorotriamide compounds can be distributed in the plant growth medium in the amount and through such cross-section of the medium as to provide for the presence therein of a urease inhibiting effective amount of the one or more phosphorotriamide compounds. It is usually preferred that the one or more phosphorotriamide compounds be distributed in the plant growth medium to a depth of at least two inches below the surface of the plant growth medium.

In another method for carrying out the present invention, one or more phosphorotriamide compounds are administered to growth medium in a band or row application. In such application, administration is made with or without carrier in amounts sufficient to supply to soil or growth medium a urease inhibiting effective amount of the one or more phosphorotriamide compounds. After administration with or without discing or dragging, subsequent irrigation or rainfall distributes the one or more phosphorotriamide compounds throughout the plant growth medium.

In one embodiment of the present invention, the one or more phosphorotriamide compounds are distributed throughout the growth media prior to seeding or transplanting the desired crop plant.

In another embodiment, the soil are the root zone of growing plants is treated with the one or more phosphorotriamide compounds in an amount effective to inhibit the action of urease, but sublethal to plant growth. By following such practice, no adverse effect is exerted by the one or more phosphorotriamide compounds upon growth of seeds or plants. Oftentimes, it is desirable to treat the soil adjacent to plants, and this procedure may be carried out conveniently in side-dressing operations.

In a further embodiment of the invention, soil or other plant growth medium is treated with one or more phosphorotriamide compounds following harvest or after, following to prevent rapid loss of urea, and to prevent buildup of soil urease. Such practice conserves the soil nitrogen for the following growing season. In such application, the upper limit is primarily an economic consideration.

In an additional embodiment, the soil or plant growth medium is impregnated with the one or more phosphorotriamide compounds in conjunction with the application of urea or one or more urea precursor compounds capable of forming urea in situ on application to the plant growth medium. Urea is a well known, commercially available compound and will not be discussed herein in detail. Illustrative of compounds which are believed to form urea on addition to the soil and are water soluble and formaldehyde condensation products, as for example methylolureas, methyleneureas and mixtures thereof. These products and a method for their preparation is described in detail in Justice U.S. Pat. No. 3,462,256. Still other useful sources of urea are water-insoluble urea formaldehyde condensation products such as ureaform. Illustrative of useful water-insoluble urea and formaldehyde condensation products are those whose preparation and use are described in detail in U.S. Pat. Nos. 3,677,746 and 4,033,745.

The amount of urea or urea precursor compound included in the composition of this invention is not critical to the unique advantages thereof, and any amount known to those of skill in the art for use in fertilizers can be used. Normally, the amount employed will vary widely depending on a number of factors, including the times and frequency of application. In the preferred embodiments of the invention, the quantity of urea or urea precursor compound may vary from about 0.5 to about 95 weight percent based on the total weight of the composition and in the particularly preferred embodiments may vary from about 1 to about 50 weight percent on the same basis. In the most preferred embodiments of this invention, the quantity of urea or urea precursor compound will vary from about 3 to about 40 weight percent on the aforementioned basis.

The fertilizer composition of this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrient and macronutrients which may be deficient in the soil. The composition may also include plant growth regulators, as for example auxins, cytokinins and the like, as well as pesticides, such as insecticides, miticides, herbicides, nematocides and the like. Moreover, the fertilizer composition can include sources of nitrogen other than urea, as for example ammonium nitrate and the like, and other materials which increase nitrogen efficiency as for example other urease inhibitors and nitrification inhibitors.

The present invention can be carried out by distributing one or more phosphorotriamide compounds in an unmodified form through a plant growth medium. The present method also embraces distributing one or more such compounds as a constituent in liquid or finely divided solid compositions. In such practice, the one or more phosphorotriamide compounds can be modified with one or more additiments or soil treating adjuvants including water, petroleum distillates or other liquid carriers, surface-active dispersing agents, and inert finely divided solids. Preferred adjuvants are surface-active dispersing agents, and inert finely divided solids; these adjuvants cooperate with the one or more phosphorotriamide compounds so as to facilitate the practice of the present invention and to obtain an improved result. Depending upon the concentration of the one or more phosphorotriamide compounds augmented compositions can be distributed in the soil without further modification or can be considered as concentrates and subsequently diluted with additional inert carrier to produce the ultimate treating composition. The urease inhibiting effective amount of the one or more phosphorotriamide compounds can be supplied to growth media in from about from 1 to about 50 gallons of organic solvent carrier, in from about 5 to about 27,000 or more gallons of aqueous carrier or in from about 20 to 2000 pounds of solids carrier per acre treated. When an organic solvent carrier is employed, it can be further dispersed in the above volume of aqueous liquid carrier.

The concentration of one or more phosphorotriamide compounds in compositions to be employed for the treatment of growth media is not critical and can vary considerably provided the required dosage of effective agent is supplied to the growth media. In general, good results are obtained with liquid and/or solid compositions containing at least about 0.00001 percent by weight of the one or more phosphorotriamide compounds. Usually, however, the weight percent of one or more phosphorotriamide compounds is from about 0.0001 percent to about 98 percent by weight of one or more phosphorotriamide compounds by weight on the same basis. In the preferred embodiments of the invention, the amount of the one or more phosphorotriamide compounds in the composition is from about 0.002 to about 50 weight percent, and in the particularly preferred embodiments is from about 0.01 to about 20 weight percent on the aforementioned basis. Liquid or dust compositions in which the one or more phosphorotriamide compounds is present in higher concentration can be utilized as such or can be employed as concentrate compositions to be diluted to prepare actual treating compositions.

Liquid compositions containing the desired amount of the one or more phosphorotriamide compounds can be prepared by dispersing the latter in one or more liquid carriers such as water or an organic solvent with or without the aid of a suitable surface active dispersing agent or emulsifying agent. Suitable organic solvents include acetone, di-isobutylketone, methanol, ethanol, isoproyl alcohol, diethyl ether, toluene, methylene chloride, chlorobenzene and the petroleum distillates. The preferred organic solvents are those which are of such volatility that they leave little permanent residue in the growth media. Dispersing and emulsifying agents which can be employed in liquid compositions include condensation products of alkylene oxides with phenols and organic acids, alkyl aryl sulfonates, polyoxyalkylene derivatives or sorbitol ester, sugar esters, complex ether alcohols, mahogany soaps and the like. The surface active agents are generally employed in the amount of from about 1 to about 20 percent by weight of one or more phosphorotriamide and preferably in an amount of from about 1 to about 10 on the same basis.

Solid compositions containing the active one or more phosphorotriamide compounds can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with a solid one or more phosphorotriamide compounds or wet with a liquid one or more phosphorotriamide compounds or a solution of dispersion of a solid or liquid one or more phosphorotriamide compounds in a volatile organic solvent. Depending upon the proportions of ingredients, these compositions can be employed without further modification or be considered concentrates and subsequently further diluted with solid surface active dispersing agent, talc, chalk, gypsum, bentonite, diatomaceous earth, fullers earth, or the like to obtain the desired treating composition. Furthermore, such concentrate compositions can be dispersed in water with or without added dispersing agent or agents to prepare aqueous soil treating compositions.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, diaper treatment, pharmaceutical applications, urease inhibition in mammalian urinary tracts, and the like. It should be noted that the particular active compound employed in one application may not necessarily be useful in another application. Thus, in the selection of a particular active material for use in an application, such factors as toxicity of the material, the environment in which the material will be used, level of urease inhibition desired and the like must be considered in selecting such material.

Phosphorotriamide compounds which are useful as urease inhibitors in the practice of this invention are those of the formula:

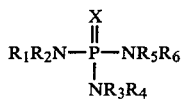

wherein:

X is sulfur or oxygen;

$R_1$ is alkyl, alkenyl, alkynyl, aralkyl, cycloalkyl or cycloalkenyl;

$R_2$ is heterocycle, aryl or aryl substituted with one or more substituents selected from the group consisting of trihalomethyl, aryloxy, alkyl, halo, alkylcarboxy, phenoxy, nitro, cyano, amino, alkylamino, dialkylamino, alkoxy, arylmercapto, mercapto, isocyanato, alkylmercapto, alkylcarbonyl, isocyano arylcarbonyl, carboxy, carbonamide, $(NH_2)_2P(O)O$—, $(NH_2)_2P(O)NH$—, $H_2NSO_2$—, 3-pyridyl, 2-furyl, benzyl and cinnamenyl; and $R_3$, $R_4$, $R_5$ and $R_6$ are individually hydrogen or alkyl having from about 1 to about 4 carbon atoms.

Illustrative of permissible $R_1$ substituents are methyl, ethyl, acetylene, propyl, isopropyl, butyl, isobutyl, allyl, pentyl, neopentyl, hexyl, heptyl, ethyl, propenyl, 2-butenyl, 3-pentenyl, 2-hexenyl, benzyl, 1-phenylpropyl, and the like.

Examples of useful $R_3$, $R_4$, $R_5$ and $R_6$ substituents are hydrogen, methyl, ethyl, propyl, isopropyl, butyl, isobutyl and the like.

Exemplary of useful $R_2$ substituents are naphthyl; heterocycle, such as 3-pyridyl and 2-furyl, phenyl, and substituted phenyl such as alkoxyphenyl as for example 2-methoxyphenyl, 3-ethoxyphenyl, 2,4-dimethoxyphenyl, and the like; alkylphenyl, as for example 2,4-dimethylphenyl, 4-ethylphenyl, 4-tert-butylphenyl, 2-methyl-4-ethylphenyl and the like; halophenyl as for example 4-chlorophenyl, 2-chloro-4-bromo phenyl, 4-idophenyl, 3-fluorophenyl and the like; 4-carboxyphenyl; alkyl- or aryl mercapto phenyl as for example 2-methylmercaptophenyl, 4-phenylmercaptophenyl, 2-ethylmercaptophenyl, 4-aminophenyl, and the like; amino, alkylamino, dialkylamino and phenylamino as for example 4-methylaminophenyl, 2,4-dimethylaminophenyl, 4-phenylaminophenyl and the like; and alkyl- and aryl carbonyl, as for example 4-acetylphenyl, 4-benzoylphenyl and the like;

The following compounds are illustrative of phosphorotriamide compounds which can be employed in the practice of this invention.

N-cyclohexyl-N-phenyl phosphoric triamide
N-cyclopropyl-N-(4-nitrophenyl) phosphoric triamide
N-methyl-N-(4-chlorophenyl) phosphoric triamide
N-propyl-N-(4-mercaptophenyl) phosphoric triamide
N-propenyl-N-(2,3-dimethylphenyl) phosphoric triamide
N-cyclopenyl-N-(4-aminophenyl) phosphoric triamide
N-methyl-N-naphthyl phosphoric triamide
N-methyl-N-(2-piperidinyl) phosphoric triamide
N-methyl-N-(β-pyrrolidinyl) phosphoric triamide
N-hexyl-N-(4-dimethylaminophenyl) phosphoric triamide
N-butyl-N-(3-methylaminophenyl) phosphoric triamide
N-benzyl-N-(4-phenylmercaptophenyl) phosphoric triamide
N-(2-phenylethyl)-N-phenyl phosphoric triamide
N-(5-phenylpentyl)-N-(2-triazinyl) phosphoric triamide
N-(cyclohexyl)-N-(4-hydroxyphenyl) phosphoric triamide
N-(allyl)-N-(3-acetylphenyl) phosphoric triamide
N-(ethyl)-N-(2,4-dimethoxyphenyl) phosphoric triamide
N-(3-hexenyl)-N-(4-acetamidophenyl) phosphoric triamide
N-(acetylene)-N-(4-trifluoromethylphenyl) phosphoric triamide
N-(3-cyclohexenyl)-N-(3-acetoxyphenyl) phosphoric triamide
N-(propyl)-N-(2,4-dichlorophenyl) phosphoric triamide
N-(ethyl)-N-(4-biphenylcarbonylphenyl) phosphoric triamide
N-cyclohexyl-N-(2,3-difluorophenyl) phosphoric triamide
N-(methyl)-N-(2,3-dibromophenyl) phosphoric triamide
N-(4-hexynyl)-N-(3-mercaptophenyl) phosphoric triamide
N-(methyl)-N-(4-phenoxyphenyl) phosphoric triamide
N-(methyl)-N-(2,3-dinitrophenyl) phosphoric triamide
N-(ethyl)-N-(4-aminophenyl) phosphoric triamide
N-(isopropyl)-N-(3-cyanophenyl) phosphoric triamide
N-(methyl)-N-(2-chloro-4-nitrophenyl) phosphoric triamide
N-(benzyl)-N-(4-methylaminophenyl) phosphoric triamide
N-(butyl)-N-(2-methyl-4-methoxyphenyl) phosphoric triamide
N-(methyl)-N-(2-trichloromethyl-4-chlorophenyl) phosphoric triamide
N-(hexyl)-N-(4-ethoxyphenyl) phosphoric triamide
N-(methyl)-N-(2-oxazinyl) phosphoric triamide
N-(methyl)-N-(3-oxazolidinyl) phosphoric triamide
N-(methyl)-N-(4-oxathiazinyl) phosphoric triamide
N-(ethyl)-N-(3-thiazinyl) phosphoric triamide
N-(methyl)-N-(2-thiazolidinyl) phosphoric triamide
N-(methyl)-N-(naphthyl) phosphoric triamide
N-(propyl)-N-(4-phenylmercaptophenyl) phosphoric triamide
N-methyl-N-(5-methylmercapto-3-triazolyl) phosporic triamide
N-(methyl)-N-(4-dimethylaminophenyl) phosphoric triamide
N-(ethyl-N-(3-diazinyl) phosphoric triamide N-ethyl-N-(2,3,4-triaminophenyl) phosphoric triamide
N-isopropyl-N-phenyl phosphoric triamide
N-methyl-N-(2-pyridyl) phosphoric triamide
N-isobutyl-N-(3-quinolinyl) phosphoric triamide
N-methyl-N-(2-pyrimidyl) phosphoric triamide
N-methyl-N-(5,6,7,8-tetrahydronaphthylenyl) phosporic triamide
N-methyl-N-(4-quinaldinyl) phosphoric triamide
N-methyl-N-pyrazinyl phosphoric triamide
N-tert-butyl-N-phenyl phosphoric triamide
N-methyl-N-(3-trichloromethyl-5-thiadiazolidyl) phosphoric triamide
N-sec-butyl-N-phenyl phosphoric triamide
N-methyl-N-(3-picolinyl) phosphoric triamide
N-ethyl-N-(5-nitropyridinyl) phosphoric triamide
N-octyl-N-phenyl phosphoric triamide
N-oleyl-N-phenyl phosphoric triamide
N-(1-isopentenyl)-N-(2,4-dimethoxyphenyl) phosphoric triamide
N-propargyl-N-phenyl phosphoric triamide
N-allyl-N-phenyl phosphoric triamide
N-methyl-N-2-[(3-methyl-(5-trichloromethyl)triazinyl] phosphoric triamide Preferred for use in the practice of this invention are compounds in which:
X is oxygen;
$R_1$ is alkyl having from 1 to about 4 carbon atoms;
$R_2$ is 3-pyridyl, 2-furyl, 2-naphthyl, cinnamenyl, benzyl, phenyl or phenyl substituted by one or more alkylmercapto nitro, cyano, hydroxy, amino, alkyl, phenoxy, alkoxy, mercapto, chloro, bromo, and fluoro; and
$R_3$, $R_4$, $R_5$ and $R_6$ are individually hydrogen, methyl or ethyl.

Particularly preferred for use in this invention are compounds in which:
$R_1$ is methyl;
$R_2$ is phenyl or phenyl substituted with 3-nitro, 4-nitro, 4-halo, 4-amino, 4-methyl, 4-cyano, 4-hydroxy, 4-trifluoromethyl, 4-trichloromethyl, 3-trifluoromethyl, 2-methyl, 2,3-dimethyl, 2,4 dimethyl, 2,4,6-trimethyl, 3-phenoxy, 3-methylmercapto, 4-methylmercapto, or 3-phenoxy; and
$R_3$, $R_4$, $R_5$ and $R_6$ are hydrogen.

Especially effacious compounds for use in the practice of this invention are N-methyl-N-phenyl phosphoric triamide, N-methyl-N-(4-methoxyphenyl) phosphoric triamide, N-methyl-N-(4-nitrophenyl) phosphoric triamide and N-methyl-N-(4-hydroxyphenyl) phosphoric triamide.

Compounds for use in the practice of this invention can be prepared in accordance with the following reaction scheme:

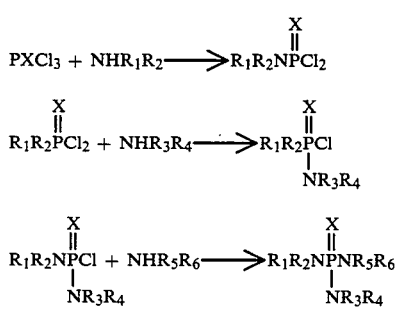

wherein X, $R_1$, $R_2$, $R_3$, $R_4$, $R_5$ and $R_6$ are as defined hereinabove.

The aforementioned reaction is described in more detail in East German Pat. No. 128,315, Roth, H. J., et al., SYNTHESIS OF PHENYL PHOSPHORODIAMIDATES. PART I., *Arch. Pharm.*, vol. 314, pp. 85-91, 1980, and references cited therein, and will not be described herein in great detail. Briefly stated, in each step of the three step reaction sequence, substantially equal molar amounts or excesses of the reactants are contacted neat or in an inert solvent, with or without a hydrogen chloride acid acceptor. Useful solvents include ethyl ether, carbon tetrachloride, methylene chloride, benzene, dioxane, toluene, xylene, and the like.

The acid acceptor employed is a basic material which can be either an inorganic or organic base. Suitable inorganic bases include alkali metal carbonates, such as sodium carbonate, potassium carbonate and the like. Organic bases which are useful and preferred for use in the practice of the invention are tertiary amines, as for example, pyridine, 1,4-diazabicyclo[2.2.2]octane, isoquinoline, trimethylamine, triethylamine, N-ethyl piperidine, quinoline, lutidine, tributylamine, and the like. Alternatively, and excess of the amine reactant can be used as the acid acceptor.

Reaction temperatures and pressures are not critical. The reaction can be conveniently carried out at a temperature of from about −20° C. to about 200° C., but is preferably carried out at a temperature of from about 25° C. to about 125° C. The reaction can be carried out at atmospheric, sub-atmospheric or super-atmospheric pressure. For convenience, however, the reaction is carried out at atmospheric or autogeneous pressure.

The order in which the reactants are reacted indicated in the reaction scheme is for illustrative purposes only, and the order of reaction is not critical. The exact proportions of the reactants are not critical, some of the desired product being obtained when the reactants are employed in any proportions. However, in going to completion, the reaction consumes the reactants and the hydrogen chloride acceptor in substantially equimolar proportions and the use of the reactants and the hydrogen chloride acceptor in such proportions is preferred.

Reaction times are not critical and can be varied widely depending on such factors as the reaction temperature, reactivity of the reactants, and the like. The reaction mixture is usually held within the desired reaction temperature range for a period of time, conveniently from about 2 to about 8 hours before cooling. Good yields are obtained with reaction times of from 4 to about 5 hours.

During the reaction, the hydrochloride salt of the hydrogen chloride acceptor forms and may precipitate from the mixture. This salt can be removed by such conventional procedures as extraction, filtration or centrifugation. The phosphorotriamide product can be separated by such conventional procedures as evaporation, and purified by conventional procedures such as distillation and extraction. The product separated as described above can be employed in the control of urease in the soil or in other applications in accordance with this invention or may be further purified by conventional procedures such as extraction and distillation.

EXAMPLE I

Preparation of N-Methyl-N-phenyl Phosphoramidic Dichloride

A 500 mL three-necked flask was fitted with an $N_2$ inlet, thermometer and dropping funnel. The flask was flushed with nitrogen and charged with 150 mL dry ether and 31.1 g (0.203 mol) $POCl_3$. In the dropping funnel was placed a solution of 21.4 g (0.20 mol) N-methylaniline in 5 mL ether. The amine solution was added to the solution of $POCL_3$ (at $-12°$ to $-17°$ C.) over 40 minutes. The temperature was allowed to rise slowly to room temperature and stirring continued for 2 h thereafter. After filtering, volatiles were removed from the filtrate at reduced pressure. The 15.4 g (69% yield) of crude product was distilled (bp 96°–98° C. at 0.05 mm).

NMR: $\delta 7.33$ (s,5H), 3.25 (d,1.5H,$J_{CH_3-N-P}=14.5$ Hz), 3.23(d) 1.5H, $J^{CH_3-N-p}=14.5$ Hz)

IR (neat): 3060, 2940, 1598, 1494, 1455, 1290, 1265, 1182, 1060, 1027, 910, 758, 710, 698 $CM^{-1}$.

EXAMPLE II

Preparation of N-Methyl-N-phenyl Phosphoric Triamide

A 250 mL flask was fitted with a dry ice condenser, thermometer and a gas inlet tube coming from a cylinder of ammonia. Methylene chloride (100 mL) was added and the solution cooled to $-30°$ to $-40°$ C. Ammonia (10.0 g, 0.59 mol) was bubbled in. The gas inlet tube was then replaced with a dropping funnel containing 8.1 g N-Methyl-N-phenyl phosphorodichloridate (0.036 mol) in 50 mL $CH_2Cl_2$. This was added over 20 min. The solution was warmed slowly to room temperature and filtered (3.8 g white solid). The solvent was removed under vacuum to give 6.5 g (98% yield) white solid, which was recrystallized from $CH_2Cl_2$. After drying over $P_2O_5$, the product had a mp of 97°–99° C. with some earlier softening.

Anal. Calcd. for $C_7H_{12}N_3OP$: C, 45.41% H, 6.53%; N, 22.69%. Found: C, 45.12%; H, 6.41%; N, 23.07%.

NMR (DMSO-$d_6$): $\delta 6.86-7.41$ (m,5H), 3.86 (bs,4H), 3.03, (d,3H,$J_{CH_3-N-P}=8.8$ Hz).

EXAMPLE III

Preparation of N-Methyl-N-methoxyphenyl) Phosphoramidic Dichloride

A 250 mL flask was flushed with nitrogen via condenser and charged with 75 mL dry ether and 18 g (0.117 mol) $POCl_3$. This was cooled to $-15°$ C. and a solution of 9.6 g (0.07 ml) N-Methyl-p-anisidine (Aldrich) in 25 mL ether was added dropwise with stirring over 45 min. The solution was warmed to room temperature and stirred 2 h more. After filtering the reaction mixture, the filtrate was distilled affording 4.0 g of a yellow liquid bp 142° C. at 0.08 mm (45% yield).

NMR (CDCl$_3$): an AA' XX' pattern from $\delta 6.8-7.3$ (4H), 3.8 (s,3H), 3.4 (d,3H, $J_{CH_3-N-p}=15$ Hz).

EXAMPLE IV

Preparation of N-Methyl-4-methyoxyphenyl) Phosphoric Triamide

In a manner as described for the preparation of N-methyl-N-phenyl phosphoric triamide, 3.7 g (0.015 mol) of N-methyl-(4-methoxyphenyl) phosphorodichloridate in 20 mL $CH_2Cl_2$ was added to 8 g $NH_3$ in 50 mL $CH_2Cl_2$. Filtration gave 3.7 g white solid and 1 g yellow solid from the filtrate. Extraction of the 3.7 g portion with $CH_2Cl_2$ gave 2.1 g (67%) of the desired product, mp 122°–124° C.

Anal Calcd. for $C_8H_{14}N_3O_2P$: C, 44.65%; H, 6.56%; N, 19.54%.

Found: C, 44.38%; H, 6.49%; N, 19.67%.

NMR (DMSO-$d_6$): AA'XX' quartet $\delta 6.7-7.25$ (4H) $\delta 3.68$ (s with bs underneath), 3.2 (bs) 2.95 (d,J=8–9 Hz). With added $D_2O$, the broad singlets collapsed into a sharp singlet at 4.65. The intentities of the bands were then 6 6.7–7.3 (8, 4H), $\delta 4.65$ (s, 4H), 3.68 (3H), 2.95 (d, 3H).

EXAMPLE V

Preparation of N-Methyl-N-(4-nitrophenyl) Phosphoramidic Dichloride p-Nitro-N-methylaniline (9.3 g, 0.061 mol) and 9 mL (0.1 mol) $POCl_3$ were heated in 50 mL toluene to 90°–95° C. overnight. The solution was cooled and filtered. The volatiles were removed from the filtrate, giving 15.3 g of a purple, viscous oil. NMR (CDCl$_3$): AA'XX' quartet from $\delta 7.45-7.35$ (4H), 3.37 (d,3H, J=14–15 Hz). No N—H was observed in the NMR. Due to an expected very high boiling point, this material was not distilled but used directly in the preparation of N-Methyl-N-(4-nitrophenyl) phosphoric triamide in the following Example VI.

EXAMPLE VI

Preparation of N-Methyl-N-(4-nitrophenyl) Phosphoric Triamide

N-Methyl-N-(4-nitrophenyl) phosphoramidic dichloride (15.3 g, 0.057 mol) was dissolved in 30 mL $CH_2Cl_2$ and added slowly to 120 mL $CH_2Cl_2$ at 0° C. containing 10 g (0.59 mol) $NH_3$. The mixture was stirred 0.5 h more at 0° C., then warmed to room temperature overnight. The reaction mixture was filtered and the yellow solid was washed with 100 mL $CH_2Cl_2$, giving 16.8 g product containing by-product $NH_4Cl$. Pure product was obtained upon Soxhlet extraction of this solid using $CH_2Cl_2$. After drying the resultant yellow solid over $P_2O_5$, it had mp 158° C. (with partial decomposition at 152° C.).

Anal. Calcd. for $C_7H_{11}N_4O_3P$: C, 36.53%; H, 4.82%; N 24.34%.

Found: C, 36.49%; H, 4.65%; N, 24.20%.

NMR (DMSO-$d_6$–$D_2O$): AA'XX' quartet from $\delta 7.4-8.2$ (4H), 4.27 (s,4H), 3.16 (d,3H,J=9 Hz).

EXAMPLES VII

Several representative N-alkyl-N-aryl phosphoric triamide compounds useful in the practice of this invention were tested to determine their relative effectiveness or urease inhibitors. The inhibition tests were run in a New York soil (Cazenovia sandy loam, pH 7.2). Evaluations (run in triplicate) consisted of applying 800 and 20 micrograms of test compound in 5 mL water and 42.8 mg urea in 1 mL water to 20 g air-dry soil in a glass bottle. The bottle was capped with perforated aluminum foil and incubated at 25° C. for 3 days prior to extraction with 100 mL 2M KCl containing 0.5 mg phenylmercuric acetate. The extracts were then analyzed for remaining urea using an auto analyzer. Percent inhibition was calculated as $$\% \; Inhibition = [-1(A-B/A-C)] \times 100$$

where A is urea recovered from unincubated sample (urea added to soil and immediately extracted); B is urea recovered from inhibited sample; and C is urea recovered from the control (uninhibited sample).

The results of these test are set forth in the following TABLE I.

TABLE I

Urease Inhibition by Phosphorotriamides, $R_1R_2NPO(NH_2)_2$

| Ex. | $R_1$ | $R_2$ | % Inhibition 800 μmg | % Inhibition 20 μmg |
|---|---|---|---|---|
| VII | $O_2N-$⌬$-$ | $-CH_3$ | 95 | 59 |
| VIII | $CH_3O-$⌬$-$ | $-CH_3$ | 47 | — |
| IX | $HO-$⌬$-$ | $-CH_3$ | 86 | — |

EXAMPLE X

Employing the procedure of EXAMPLES VII to IX a series of test were conducted to show improved efficiency of N-aliphatic-N-arylphosphoric triamides at elevated temperature as compared to the efficiency of phenylphosphorodiamidate, a prior art urease inhibitor. This test was conducted similarly to the test previously described, but soil samples were taken every two days and analyzed for urea content. The results of these tests are set forth in the FIGURE.

The FIGURE shows that N-methyl-N-(4-nitrophenyl) phosphoric triamide is an excellent inhibitor even when soil temperatures are 35° C.(95° F.) for a period of 12 days. By comparison, phenyl phosphorodiamidate, a known compound which has an excellent urease inhibiting effect at 25° C., is much less effective at 35° C., allowing essentially complete urea hydrolysis after only 6 days.

EXAMPLE XI

Employing the procedure of EXAMPLES VII to IX a series of test were conducted to illustrate the superior efficacy of the N-aliphatic-N-aryl phosphoric triamide compounds used in the practice of the inventors as compared to other N-arylphosphoric triamide compounds. The results of these tests are set forth in the following TABLE II.

TABLE II

Urease Inhibitors by Phosphorotriamide, $R_1R_2PO(NH_2)_2$

| Ex. | $R_1$ | $R_2$ | % Inhibition 800 μmg | % Inhibition 20 μmg |
|---|---|---|---|---|
| VII | $O_2N-$⌬$-$ | $-CH_3$ | 95 | 59 |
| Comp I | $O_2N-$⌬$-$ | $H-$ | 81 | 30 |
| Comp II | $H-$⌬$-$ | $H-$ | 74 | 19 |

What is claimed is:

1. A urease inhibiting composition comprising an acceptable carrier and a urease inhibiting effective amount of one or more phosphorotriamide compounds of the formula:

$$R_2-\underset{\underset{NR_3R_4}{|}}{\overset{\overset{R_1}{|}}{N}}-\overset{\overset{X}{\|}}{P}-NR_5R_6$$

wherein:
X is oxygen or sulfur;
$R_1$ is alkyl, alkenyl, alkynyl, cycloalkyl, cycloalkenyl or aralkyl;
$R_2$ is heterocycle, aryl, or aryl substituted with one or more substituents selected from the group consisting of trihalomethyl, alkyl, halo, phenoxy, phenyl, nitro, cyano, amino, alkylamino, dialkylamino, alkoxy, amido, mercapto, alkylmercapto, arylmercapto, alkylcarbonyl, arylcarbonyl, quaternary ammonium radicals, carboxy, alkylcarboxy, carbonamide, isocyano, isocyanato, $(NH_2)_2P(O)O-$, and $(NH_2)_2P(O)NH-$, $H_2NSO_2-$; and
$R_3$, $R_4$, $R_5$ and $R_6$ are individually hydrogen or alkyl having from 1 to 4 carbon atoms.

2. A composition according to claim 1 wherein said urease inhibiting amounts is at least about 0.00001 weight percent based on the total weight of the composition.

3. A composition according to claim 2 wherein said amount is from about 0.0001 to about 98 weight percent.

4. A composition according to claim 3 wherein said amount is from about 0.002 to about 50 weight percent.

5. A composition according to claim 4 wherein said amount is from about 0.01 to about 20 weight percent.

6. A composition according to claim 1 wherein X is oxygen.

7. A composition according to claim 1 wherein $R_1$ is alkyl.

8. A composition according to claim 7 wherein $R_1$ is methyl, ethyl or propyl.

9. A composition according to claim 8 wherein $R_1$ is methyl.

10. A composition according to claim 1 wherein $R_2$ is substituted aryl.

11. A composition according to claim 10 wherein $R_2$ is substituted phenyl.

12. A composition according to claim 11 wherein $R_2$ is phenyl substituted with one or more substituents selected from the group consisting of nitro, mercapto, hydroxy, trihalomethyl, cyano, halo, amino, alkyl, alkylamino, dialkylamino, phenyl, alkoxy or phenoxy.

13. A composition according to claim 12 wherein said phenyl is substituted with 1, 2 or 3 substituents.

14. A composition according to claim 13 wherein said phenyl is substituted with one or two substituents at the ortho position, para position or ortho and para position.

15. A composition according to claim 14 wherein said phenyl is substituted at the para position with nitro, alkoxy or hydroxy substituents.

16. A composition according to claim 15 wherein said phenyl is substituted by 3-nitro, 4-nitro, 4-methylmercapto, 4-halo, 4-amino, 4-alkyl, 4-alkoxy, 2-methyl, 2,3-dimethyl, 4-hydroxy, 2,4-dimethyl, 2,4,6-trimethyl, 3-trihalomethyl, 4-cyano, 4-phenyl or 3-phenoxy.

17. A composition according to claim 1 wherein $R_2$ is unsubstituted aryl.

18. A composition according to claim 7 wherein $R_2$ is phenyl.

19. A composition according to claim 1 wherein $R_3$, $R_4$, $R_5$ and $R_6$ are individually hydrogen or methyl.

20. A composition according to claim 19 wherein $R_3$, $R_4$, $R_5$ and $R_6$ are hydrogen.

21. A composition according to claim 1 wherein said one or more phosphorotriamide compounds are selected from the group consisting of [N-methyl(4-aminophenyl)]phosphorotriamide, [N-methyl-N-(4-cyanophenyl)]phosphorotriamide, [N-methyl-N-(3-trifluoromethylphenyl)]phosphorotriamide, [N-methyl-N-(4-hydroxyphenyl)]phosphorotriamide, [N-methyl-N-phenyl]phosphorotriamide, [N-methyl-N-(4-methoxyphenyl)]phosphorotriamide and [N-methyl-N-(4-nitrophenyl)]phosphorotriamide.

22. A composition according to claim 21 wherein said phosphorotriamide compound is [N-methyl-N-(4-nitrophenyl)]phosphorotriamide, [N-methyl-N--(4-hydroxyphenyl)]phosphorotriamide, [N-methyl-N-phenyl]phosphorotriamide, or [N-methyl-N-(4-methoxyphenyl)]phosphorotriamide.

23. A composition according to claim 22 wherein said phosphorotriamide compound is [N-methyl-N-(4-nitrophenyl)]phosphorotriamide.

24. A method of inhibiting the urease catalyzed hydrolysis of urea at a situs which comprises applying to said situs a urease inhibiting effective amount of one or more phosphorotriamide compounds of the formula:

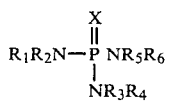

wherein:
$R_1$ is alkyl, alkenyl, cycloalkyl, cycloalkenyl or aralkyl;
$R_2$ is heterocycle, aryl or aryl substituted with one or more substituents selected from the group consisting of trihalomethyl, alkyl, halo, phenoxy, phenyl, nitro, cyano, amino, alkylamino, dialkylamino, alkoxy, amido, mercapto, alkylmercapto, arylmercapto, alkylcarbonyl, arylcarbonyl, quaternary amonium radicals, carboxy, alkylcarboxy, carbonamide, isocyano, isocyanato, $(NH_2)_2P(O)O-$, $(NH_2)_2P(O)NH-$ and $H_2NSO_2-$; and $R_3$, $R_4$, $R_5$ and $R_6$ are individually hydrogen or alkyl having from 1 to 4 carbon atoms.

25. A method according to claim 24 wherein said compounds is applied to said situs, prior to, in conjunction with or subsequent to application of urea or a compound capable of forming urea in situ to said situs.

26. A method according to claim 25 wherein said situs is a plant growth medium.

27. A method according to claim 26 where said compound is applied to said medium not more than about 10 days after application of said urea or said compound.

28. A method according to claim 27 where said compound is applied to said medium, not more than about 5 days after application of said urea or said compound.

29. A method according to claim 28 where said compound is applied to said medium not more than about 2 days after application of said urea or said compound.

30. A method according to claim 24 wherein said urease inhibiting effective amount is at least about 0.01 p.p.m.

31. A method according to claim 30 wherein said amount is from about 0.01 p.p.m. to about 5,000 p.p.m.

32. A method according to claim 31 wherein said amount is from about 0.2 p.p.m. to about 1000 p.p.m.

33. A method according to claim 32 wherein said amount is from about 1 p.p.m. to about 500 p.p.m.

34. An improved fertilizer composition which comprises urea and/or one or more urea precursor compounds capable of forming urea in situ when subjected to the use condition of the composition and a urease inhibiting effective amount of one or more phosphorotriamide compounds of the formula:

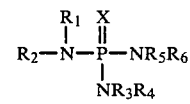

wherein:
X is oxygen or sulfur;
$R_1$ is alkyl, alkenyl, alkynyl, cycloalkyl, cycloalkenyl, or aralkyl;
$R_2$ is heterocycle, aryl, or aryl substituted with one or more substituents selected from the group consisting of trihalomethyl, alkyl, halo, amido, phenoxy, phenyl, nitro, cyano, amino, alkylamino, dialkylamino, alkoxy, alkylcarboxy, mercapto, isocyano, alkylmercapto, arylmercapto, alkylcarbonyl, isocyanato, arylcarbonyl, quaternary ammonium radicals, carboxy, carbonamide, $(NH_2)_2P(O)O-$, $(NH_2)_2P(O)NH-$ or $H_2NSO_2-$; and
$R_3$, $R_4$, $R_5$ and $R_6$ are individually hydrogen or alkyl having from 1 to 4 carbon atoms.

35. A method of enhancing plant growth and crop yield which comprises applying an effective amount of the composition according to claim 34 to the plant growth medium within the root zone of the plant.

36. A composition according to claim 1 wherein said carrier is a liquid.

37. A composition according to claim 36 wherein said liquid carrier is selected from the group consisting of water and organic liquids.

38. A composition according to claim 1 wherein said carrier is a finely divided inert solid.

39. A composition according to claim 1 wherein X is sulfur.

* * * * *